United States Patent [19]

Senbo

[11] Patent Number: 5,567,429
[45] Date of Patent: Oct. 22, 1996

[54] PEST CONTROLLING COMPOSITION

[75] Inventor: Satoshi Senbo, Takarazuka, Japan

[73] Assignee: Sumitomo Chemical Company, Limited, Osaka, Japan

[21] Appl. No.: 360,637

[22] Filed: Dec. 21, 1994

[30] Foreign Application Priority Data

Dec. 21, 1993 [JP] Japan .................................. 5-322151

[51] Int. Cl.⁶ .................................................. A01N 43/50
[52] U.S. Cl. ........................... 424/405; 424/43; 424/401; 424/403; 424/405; 424/408
[58] Field of Search ..................... 424/401, 403, 424/405, 43, 408

[56] References Cited

U.S. PATENT DOCUMENTS

| 5,122,530 | 6/1992 | Tomioka et al. | 514/341 |
| 5,153,215 | 10/1992 | Tomioka et al. | 514/396 |
| 5,232,940 | 8/1993 | Hatton et al. | 514/407 |

FOREIGN PATENT DOCUMENTS

| 0295117 | 6/1988 | European Pat. Off. . |
| 0435609 | 7/1991 | European Pat. Off. . |
| 0445931 | 9/1991 | European Pat. Off. . |

OTHER PUBLICATIONS

Chem Ab 120:71572, "Resin compositions for controlling harmful insects," Chinuki, Takashi et al. (Sumitomo Chemical Co, Japan), JP 92–281334 9210 20.
Chemical Abstracts, vol. 118, No. 23, Abtract No. 228183 (Jun. 7, 1993).

Primary Examiner—Thurman K. Page
Assistant Examiner—Sharon Howard
Attorney, Agent, or Firm—Cushman Darby & Cushman, L.L.P.

[57] ABSTRACT

The present invention relates to a pest controlling composition containing as active ingredients at least one insect growth regulator and at least one N-aryldiazole compound selected from the group consisting of 4-(2-bromo-1,1,2,2-tetrafluoroethyl)-1-(3-chloro-5-trifluoromethylpyridine-2-yl)-2-methylimidazole, 5-amino-3-cyano-1-(2,6-dichloro-4-trifluoromethylphenyl)-4-trifluoromethylsulfinylpyrazole and 5-amino-3-cyano-1-(2,6-dichloro-4-trifluoromethylphenyl)-4-trifluoromethylthiopyrazole.

The pest controlling composition of the present invention shows very excellent pest controlling effect.

14 Claims, No Drawings

PEST CONTROLLING COMPOSITION

The present invention relates to a pest controlling composition for controlling various kinds of pest such as sanitary pests (e.g. flies, mosquitoes, cockroaches and mites), and blood-sucking pests such as ticks, fleas, etc. which are parasites on animals (e.g. pets). The object of this invention is to provide a novel composition showing an excellent pest controlling effect at a low dosage.

The present invention provides a composition having an excellent pest controlling activity, and said composition is a pest controlling composition (hereinafter referred to as present composition) containing as active ingredients at least one insect growth regulator and at least one N-aryldiazole compound selected from the group consisting of 4-(2-bromo-1,1,2,2-tetrafluoroethyl)-1 -(3-chloro-5-trifluoromethylpyridine-2-yl)-2-methylimidazole (hereinafter referred to as compound A) of the formula:

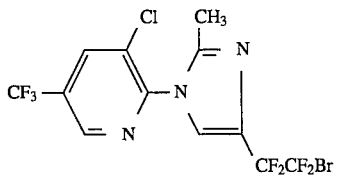

5-amino-3-cyano-1(2,6-dichloro-4-trifluoromethyl-phenyl)-4-trifluoromethylsulfinylpyrazole (hereinafter referred to as compound B) of the formula:

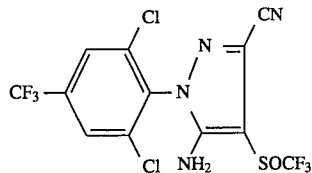

and 5-amino-3-cyano-1-(2,6-dichloro-4-trifluoromethylphenyl-4-trifluoromethylthiopyrazole (hereinafter referred to as compound C) of the formula:

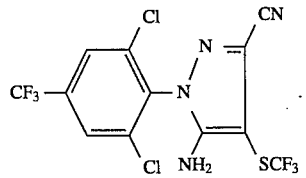

The present composition containing as active ingredients at least one insect growth regulator and at least one N-aryldiazole compound selected from the group consisting of compounds A, B and C shows excellent pest controlling effect against various pests such as sanitary pests and blood-sucking pests at a low dosage.

Said N-aryldiazole compound is known as described in U.S. Pat. No. 5,122,530 and EP 295,117 and may be prepared according to said patents.

The insect growth regulator used in the present invention includes, for example, juvenile hormone-active compounds and chitin synthesis inhibitors described below.

The juvenile hormone-active compounds include, for example, the following:
(1) 4-phenoxyphenyl 2-(2-pyridyloxy)propyl ether [pyriproxyfen],
(2) ethyl 2-(4-phenoxyphenoxy)ethyl carbamate [fenoxycarb],
(3) isopropyl (2E,4E)-11-methoxy-3,7,11-trimethyl-2,4-dodecadienoate [methoprene],
(4) 4-chloro-2-(2-chloro-2-methylpropyl)-5-(6-iodo-3-pyridylmethoxy)pyridazine-3 (2H)-one, and
(5) ethyl (2E,4E)-3,7,11-trimethyl-2,4-dodecadienoate [hydroprene].

The chitin synthesis inhibitors include, for example, the following:
(6) 2-tert-butylimino-3-isopropyl-5-phenyl-3,4,5,6-tetrahydro -2H-1,3,5-thiadiazine-4-one,
(7) N-cyclopropyl-1,3,5-triazine-2,4,6-triamine [cyromazine]and, benzoylurea compounds described below:
(8) 1-(2,6-difluorobenzoyl)-3-[2-fluoro-4-(trifluoromethyl)phenyl]urea,
(9) 1-(4-chlorophenyl)-3-(2,6-difluorobenzoyl)urea [diflubenzuron],
(10) 1-[3,5-dichloro-4-(3-chloro-5-trifluoro-methylpyridine-2yloxy) phenyl]-3-(2,6-difluorobenzoyl)-urea [chlorofluazuron],
(11) 1-(2-chlorobenzoyl)-3-(4-trifluoromethoxyphenyl)urea [triflumuron],
(12) 1-[4-(2-chloro-4-trifluoromethylphenoxy)-2-fluorophenyl]-3-(2,6-difluorobenzoyl) urea [flufenoxuron],
(13) 1-[α-(4-chloro-α-cyclopropylbenzylideneaminooxy)-p-tolyl]-3-(2,6-difluorobenzoyl)urea [flucycloxuron],
(14) 1-[3,5-dichloro-4-(1,1,2,2-tetrafluoroethoxy)phenyl]-3-(2,6-difluorobenzoyl)urea [hexaflumuron],
(15) 1-(2,6-difluorobenzoyl)-3-[2-fluoro-4-(1,1,2,2tetrafluoroethoxy)phenyl]urea,
(16) 1-(2,6-difluorobenzoyl)-3-[2-fluoro-4-(trifluoromethyl)phenyl]urea,
(17) 1-[2,5-dichloro-4-(1,1,2,3,3,3-hexafluoropropoxy)phenyl]-3-(2,6-difluorobenzoyl)urea [lufenuron], and the like.

In the present composition, the composition containing the compound B and the insect growth regulator (1) or (8) is preferable.

In the present composition, the mixing ratio of the insect growth regulator and the above N-aryldiazole compound is usually in the range of 70:30 to 30:70 by weight.

The present composition has an excellent pest controlling activity on various kinds of pest and may be used to control, for example, Insecta which includes pests belonging to Diptera such as common mosquito (*Culex pipiens pallens*), chironomid midge (Chironomidae), housefly (Muscidae), moth fly (Psychodidae) and *Tabanus trigonus*, pests belonging to Dictyoptera such as German cockroach (*Blattella germanica*), smokybrown cockroach (*Periplaneta fuliginosa*) and American cockroach (*Periplaneta americana*), pests belonging to Hymenoptera such as hornets (Vespidae), sawfly (Tenthredinidae) and little red ants (*Monomarium pharaonis*), pests belonging to Isoptera such as *Reticulitermes speratus* and Formosan subterranean termite (*Coptotermes formosanus*), pests belonging to Orthoptera such as rice grasshoppers and camel crickets (Phaphidophoridae), pests belonging to Hemiptera such as brown rice planthopper (*Nilaparvata lugens*), greenhouse whitefly (*Trialeurodes vaporariorum*), green peach aphid (*Myzus persicae*), brown marmorated stink bug (*Halyomorpha mista*) and cimices, pests belonging to Coleoptera such as skin beetles (Dermestidae) and maize weevil (*Sitophilus zeamais*), pests belonging to Lepidoptera such as small white butterfly (*Pieris rapae crucivora*) and *Ephhestia cautella*, pests belonging to Siphonaptera such as cat flea (*Ctenocephalides felis*), dog flea (*Ctenocephalides canis*), oriental rat flea (*Xenopsylla cheopis*) and human flea (*Pulex irritans*), and pests belonging to Thysanura such as oriental silverfish (*Ctenolepisma villosa*), Arachnida which includes various kinds of mites and ticks, and spiders, Chilopoda which includes various kinds of millipedes and centipedes, and Diplopoda which includes millipedes.

The present composition may be usually used by mixing the active ingredient compounds with solid or liquid carrier, if necessary adding to the resulting mixture a surface active agent and other auxiliaries for formulation and formulating it into an oil formulation, emulsifiable concentrate, dust, smoking formulation, aerosol, liquefied carbon dioxide gas formulation, poisonous bait, resin formulation, etc.

The active ingredient compounds are usually contained in these compositions in a total amount of 0.001 to 95 wt. %.

The solid carriers used in formulation include, for example, fine powders or granules of clays (e.g. kaolin clay, diatomaceous earth, bentonite, terra abla), synthetic hydrated silicon dioxide, talcs, ceramics, other inorganic minerals (e.g. sericite, quartz, sulfur, activated carbon, calcium carbonate, hydrated silica), or chemical fertilizers (ammonium sulfate, ammonium phosphate, ammonium nitrate, urea, ammonium chloride). The liquid carriers include, for example, water, alcohols (e.g. methanol, ethanol), ketones (e.g. acetone, methyl ethyl ketone), aromatic hydrocarbons (e.g. xylene, toluene), aliphatic hydrocarbons (e.g. hexane, kerosene, paraffin, petroleum benzine), esters (e.g. ethyl acetate, butyl acetate), ethers (e.g. tetrahydrofuran, dioxane) or halogenated hydrocarbons (e.g. dichloroethane, trichloroethane, carbon tetrachloride, methylene chloride).

If necessary, the active ingredient compounds can also be formulated by mixing with a propellant such as freon gas, propane gas, butane gas, liquefied petroleum gas, dimethyl ether and carbon dioxide gas.

The surface active agents used in the present invention include, for example, alkyl sulfates, alkylarylsulfonates, alkyl aryl ethers and their polyoxyethylenated products, polyethylene glycol ethers, polyhydric alcohol esters or sugar alcohol derivatives.

Other auxiliaries for formulation such as adhesive agents and dispersing agents include, for example, casein, gelatin, saccharides (e.g. starch, gum arabic, cellulose derivatives, alginic acid), lignin derivative, bentonite or synthetic water-soluble polymers (e.g. polyvinyl alcohol, polyvinyl pyrrolidone, polyacrylic acids). Further, stabilizers such as isopropyl acid phosphate (PAP), 2,6-di-tert-butyl-4-methylphenol (BHT), a mixture of 2-tert-butyl-4-methoxyphenol and 3-tert-butyl-4-methoxyphenol (BHA), vegetable oils, mineral oils, fatty acids, fatty acid esters, etc. are also used as the auxiliary for formulation.

The base material used for the resin formulations includes, for example, vinyl chloride polymers or polyurethane. If necessary, to these base materials may be added plasticizers such as phthalic acid esters (e.g. dimethyl phthalate, dioctyl phthalate), adipic acid esters and stearic acid. The resin formulation may be obtained by kneading the active ingredient compounds, the base materials, and other ingredients if necessary using a conventional kneader, and molding the resulting kneaded products with injection molding, extrusion molding, press molding or the like. Said resin formulation may be properly formed into a pest-controlling collar for animals via steps such as molding and cutting.

The bait substance and attracting substance used in poisonous baits include, for example, cereal powders such as flour and corn powder, starches such as potato starch and corn starch, sugars such as granulated sugar, maltose and honey, glycerin, food flavors such as onion flavor, milk flavor, butter flavor and strawberry flavor, animal powders such as chrysalis powder, fish meal and krill powder, various pheromones and the like.

The present compositions thus obtained are used as they are or diluted with water, etc. The emulsifiable concentrates, etc. are generally applied in the form of their aqueous dilute solutions produced by diluting with water so as to contain about 1 to about 10000 ppm by weight of the total amount of the active ingredient compounds. The oil formulations, aerosols, smoking formulations, resin formulations, poisonous baits, etc. are applied as they are.

The dosage of the present composition applied varies with the kind of target pests to be controlled, kind of the formulations, where and how the compositions are applied, and the like. Generally, however, the dosage is about 0.0001 to about 10 $g/m^2$ in the total amount of the active ingredient compounds.

The present invention will be illustrated more specifically with reference to the formulation examples and test examples, but the present invention is not to be interpreted as being limited to these examples only.

FORMULATION EXAMPLE 1

0.1 Part by weight of the N-aryldiazole compound and 0.1 part by weight of the insect growth regulator are dissolved in 59.8 parts by weight of a deodorized kerosene, and the resulting solution is put in an aerosol container. A valve portion is attached to the aerosol container, and 40.0 parts by weight of a propane gas is charged under pressure into the aerosol container through the valve portion to obtain an oil based aerosol.

FORMULATION EXAMPLE 2

0.2 Part by weight of the N-aryldiazole compound and 0.2 part by weight of the insect growth regulator are dissolved in 14.6 parts by weight of a deodorized kerosene. To this solution are added 40.0 parts by weight of methylene chloride and 17.0 parts by weight of 1,1,1-trichloroethane, and the resulting solution is put in an aerosol container. A valve portion is attached to the aerosol container, and 28.0 parts by weight of a propane gas is charged under pressure into the aerosol container through the valve portion to obtain an oil based total release aerosol.

FORMULATION EXAMPLE 3

68.0 Parts by weight of dextrin, 5.0 parts by weight of a sesame oil, 20.0 parts by weight of a raw sugar, 5.0 parts by weight of water, 1.0 part by weight of the N-aryldiazole compound and 1.0 part by weight of the insect growth regulator are mixed and well stirred with a mixer. The resulting mixture is formed into tablets by a tableting machine under a tableting pressure of 6 tons to obtain a poisonous bait.

FORMULATION EXAMPLE 4

To a heating mixer are added 5.0 parts by weight of the N-aryldiazole compound, 5.0 parts by weight of the insect growth regulator, 57.0 parts by weight of polyvinyl chloride, 29.i6 parts by weight of dioctyl adipate, 3.0 parts by weight of an epoxidated soybean oil and 0.4 part by weight of stearic acid, and the mixture is stirred and mixed under heating. The resulting mixture is heated to 70° C., stirred for 30 minutes, supplied to an extruder, hot-cut while extruded and molded into a shape of 3 mm (thickness)×10 mm (width)×35 cm (length). A buckle is attached to this molded product to obtain a pest controlling collar for pets.

The effect of the present compositions is specifically shown with reference to the following test examples. In the examples, the insect growth regulator and N-aryldiazole compound are shown by the compound number and compound symbol, respectively, described above.

TEST EXAMPLE 1

Five parts by weight of a mixture of the N-aryldiazole compound S and insect growth regulator (8) in a predetermined weight ratio, 10 parts by weight of Sorpol SM 200 (a surface active agent containing alkyl phenol ethoxylate, alkyl phenol ethoxylate polymer, caster oil ethoxylate and dodecylbenzene sulfonate, produced by Toho Kagaku Co., Ltd.) and 85 parts by weight of xylene were mixed to obtain an emulsifiable concentrate.

This emulsifiable concentrate was diluted with distilled water to be $1/250$ concentration of it, and the resulting dilute solution was applied with a pipette onto six pieces of a decorative laminate of 15 cm×15 cm×0.3 cm at a rate of 50 ml/m$^2$ per laminate.

Baits and water were placed at two corners on the diagonal line on the bottom of a test container of 2.0 m×1.25 m in the bottom surface and 0.15 m in height, and three pieces of the decorative laminate were placed at each corner so as to enclose the baits and water. After one day and 16 weeks, ten each of the first, second and third instar larvae of German cockroach (*Blattella germanica*) and six adults thereof (three males and three females having an egg-case) were liberated in the test container.

The number of the living adults and larvae of German cockroach was counted at intervals of two weeks from 2 weeks to 24 weeks after liberation of the cockroaches. The total number of the cockroaches is shown in Table 1.

TABLE 1

| Mixing ratio of compound (8)/ compound B | Number of cockroaches | | | | Total number of cockroaches |
|---|---|---|---|---|---|
| | First instar larvae | Second instar larvae | Third instar larvae | Adults | |
| 100/0 | 455 | 247 | 13 | 93 | 808 |
| 70/30 | 198 | 106 | 26 | 71 | 401 |
| 50/50 | 259 | 107 | 26 | 53 | 445 |
| 30/70 | 246 | 138 | 27 | 45 | 456 |
| 0/100 | 456 | 218 | 68 | 104 | 846 |

As can be seen from the above table, the controlling effect obtained by using the composition containing compound (8) and compound B is nearly two times as compared with that obtained by using the compound (8) only or compound B only at the same dosage.

TEST EXAMPLE 2

One part by weight of a mixture of the N-aryldiazole compound B and insect growth regulator (8) in a predetermined weight ratio, 12 parts by weight of flour, 35 parts by weight of glucose, 7 parts by weight of a chrysalis powder, 10 parts by weight of water and 35 parts by weight of powdered sugar were mixed to obtain a poisonous bait.

The poisonous bait obtained was scattered on the floor of a pigpen so that the dosage was 1 g/m$^2$, and the number of houseflies (*Musca domestica*) sitting on the previously determined place (the handrail, etc. of the pigpen cage) was counted before application of the poisonous bait and one day, four weeks and eight weeks after application of the poisonous bait. An extermination rate was calculated according to the following equation using the mean value of the numbers of houseflies after application of the poisonous bait, Extermination rate (%) =

$$\frac{\text{Number of houseflies before application of the poisonous bait} - \text{number of houseflies after application of the poisonous bait}}{\text{number of houseflies before application of the poisonous bait}} \times 100.$$

The results are shown in Table 2.

TABLE 2

| Mixing ratio of compound (8)/compound B | Extermination rate (%) |
|---|---|
| 100/0 | 48.1 |
| 50/50 | 89.2 |
| 0/100 | 40.2 |

As can be seen from the above table, the controlling effect obtained by using the composition containing compound (8) and compound B is nearly two times as compared with that obtained by using the compound (8) only or compound B only at the same dosage.

TEST EXAMPLE 3

5 Parts by weight of a mixture of N-aryldiazole compound B and insect growth regulator (1) in a predetermined weight ratio, 10 parts by weight of Sorpol SM 200 as mentioned above and 85 parts by weight of xylene were mixed to obtain an emulsifiable concentrate.

Said emulsifiable concentrate was diluted with distilled water to be a pre-determined concentration, and 10 ml of the resulting dilute solution were applied with a pipette to 5 g of medium for houseflies (bran: powder of mouse=7:1) and the mixture was uniformly kneaded. The kneaded mixture was charged in a 100 cc polyethylene-cup and successively 30 larvae of houseflies (a strain resistant to pyrethroid and organophosphorus agent) were liberated in said cup. The upper of the cup was capped with a nylon net and the cup was stored under a room temperature. After 2 weeks of the treatment, the number of adult emergence was counted, and corrected emergence inhibition rate was calculated according to the following equation. The number of adult emergence when only distilled water was applied onto medium for houseflies was employed as a control. Each experiment was repeated twice.

Corrected emergence inhibition rate (%) =

$$\frac{(\text{the number of adult emergence without treatment} - \text{the number of adult emergence with treatment})}{\text{the number of adult emergence without treatment}} \times 100$$

TABLE 3

| Mixing ratio of compound (1)/ compound B | Corrected emergence inhibition rate % (bottom column) in each concentration, ppm (upper column) | | | | | IC$_{50}$ (ppm)* |
|---|---|---|---|---|---|---|
| 1/1 | 5.0 | 2.5 | 1.25 | 0.625 | | 0.998 |
| | 95.7 | 91.3 | 65.2 | 23.9 | | |
| 1/2 | 5.0 | 2.5 | 1.25 | 0.625 | 0.313 | 0.823 |
| | 84.8 | 80.4 | 56.5 | 47.8 | 23.9 | |

*IC$_{50}$ (ppm): concentration required to cause emergence inhibition in 50% of the test insects

What is claimed is:

1. A pest controlling composition containing as active ingredients at least one insect growth regulator and at least one N-aryldiazole compounds selected from the group consisting of 4-(2-bromo-1,1,2,2-tetrafluoroethyl)-1-(3-chloro-5-trifluoromethylpyridine-2-yl)-2methylimidazole, 5-amino-3-cyano-1-(2,6-dichloro-4-trifluoromethylphenyl)-4-trifluoromethylsulfinylpyrazole and 5-amino-3-cyano-1-(2,6-dichloro-4-trifluoromethyl-phenyl)-4-trifluoromethylthiopyrazole.

2. A pest controlling composition according to claim 1, wherein the insect growth regulator is a juvenile hormone-active compound.

3. A pest controlling composition according to claim 1, wherein the insect growth regulator is 4-phenoxyphenyl 2-(2-pyridiloxy)propylether.

4. A pest controlling composition according to claim 1, wherein the insect growth regulator is 1-(2,6-difluorobenzoyl)-3-[2-fluoro-4-(trifluoromethyl)phenyl]urea.

5. A pest controlling composition according to any of claims 1 to 4, wherein the N-aryldiazole compound is 5-amino-3-cyano-1-(2,6-dichloro-4-trifluoromethylphenyl)-4-trifluoromethylsulfinylpyrazole.

6. A pest controlling composition according to claim 1, wherein the mixing ratio of the insect growth regulator to the N-aryldiazole compound is 70:30 to 30:70 by weight.

7. A pest controlling composition according to claim 1, wherein the insect growth regulator is 2-tert-butylimino-3-isopropyl-5-phenyl-3,4,5,6-tetrahydro-2 H-1,3,5-thiadiazine-4-one, N-cyclopropyl-1,3,5-triazine-2,4,6-triamine, 1-(2,6-difluorobenzoyl)-3-[2-fluoro-4-(trifluoro-methyl)phenyl]urea, 1-(4-chlorophenyl)-3-(2,6-difluorobenzoyl)urea, 1-[3,5-dichloro-4-(3-chloro-5-trifluoromethylpyridine-2-yloxy)phenyl]-3-(2,6-difluorobenzoyl)urea, 1-(2-chlorobenzoyl)-3-(4-trifluoromethoxyphenyl)urea, 1-[4-(2-chloro-4-trifluoromethylphenoxy)-2-fluoro-phenyl]-3-(2,6-difluorobenzoyl)urea, 1-[α-(4-chloro-α-cyclopropylbenzylideneaminooxy)-p-tolyl]-3-(2,6difluorobenzoyl)urea, 1-[3,5-dichloro-4-(1,1,2,2-tetrafluoroethoxy)-phenyl]-3-(2,6-difluorobenzoyl)urea, 1-(2,6-difluorobenzoyl)-3-[2-fluoro-4-(1,1,2,2-tetra-fluoroethoxy)phenyl]urea, 1-(2,6-difluorobenzoyl)-3-[2-fluoro-4-(trifluoro-methyl)phenyl]urea, or 1-[2,5-dichloro-4-(1,1,2,3,3,3-hexafluoropropoxy)-phenyl]-3-(2,6-difluorobenzoyl)urea.

8. A pest controlling composition according to claim 7, wherein the N-aryldiazole compound is 5-amino-3-cyano-1-(2,6-dichloro-4-trifluoromethylphenyl)-4-trifluoromethylsulfinylpyrazole.

9. A pest controlling composition according to claim 7 or 8, wherein the insect growth regulator is 1-(2,6-difluorobenzoyl)-3-[2-fluoro-4-(trifluoromethyl)pheny]urea.

10. A pest controlling composition according to claim 1 or 8, wherein the insect growth regulator and the N-aryidiazole compound are mixed in a ratio of 70:30 to 30:70 by weight, and the insect growth regulator is 1-(2,6-difluorobenzoyl)-3-[2-fluoro-4-(trifluoro-methyl)pheny]urea.

11. A pest controlling composition according to claim 7 or 8, wherein the insect growth regulator and the N-aryldiazole compound are mixed together at a ratio of 70:30 to 30:70 by weight.

12. A pest controlling composition according to claim 1, wherein the insect growth regulator is 1-(2,6-difluorobenzoyl)-3-[2-fluoro-4-(trifluoromethyl)phenyl]urea, 1-(4-chlorophenyl)-3-(2,6-difluorobenzoyl)urea, 1-[3,5-dichloro-4-(3-chloro-5-trifluoromethylpyridine-2-yloxy)phenyl]-3-(2,6-difluorobenzoyl)urea, 1-(2-chlorobenzoyl)-3-(4-trifluoromethoxyphenyl)urea, 1-[4-(2-chloro-4-trifluoromethylphenoxy)-2-fluoro-phenyl]-3-(2,6-difluorobenzoyl)urea, 1-[α-(4-chloro-α-cyclopropylbenzylideneaminooxy)-p-tolyl]-3-(2,6difluorobenzoyl)urea, 1-[3,5-dichloro-4-(1,1,2,2-tetrafluoroethoxy)phenyl]-3-(2,6-difluorobenzoyl)urea, 1-(2,6-difluorobenzoyl)-3-[2-fluoro-4-(1,1,2,2-tetrafluoroethoxy)phenyl]-3-(2,6-difluorobenzoyl)urea, 1-(2,6-difluorobenzoyl)-3-[2-fluoro-4-(trifluoro-methyl)phenyl]urea, or 1-[2,5-dichloro-4-(1,1,2,2,3,-hexafluoropropoxy)-phenyl]-3-(2,6-difluorobenzoyl)urea.

13. A pest controlling composition according to claim 12, wherein the N-aryldiazole compound is 5-amino-3-cyanol-1-(2,6-dichloro-4-trifluoromethylphenyl)-4-trifluoromethylsulfinylpyrazole.

14. A pest controlling composition according to claim 12 or 13, wherein the insect growth regulator and the N-aryldiazole compound are mixed in a ratio of 70:30 to 30:70 by weight.

* * * * *